(12) United States Patent
Jun

(10) Patent No.: US 9,387,046 B2
(45) Date of Patent: Jul. 12, 2016

(54) TREATMENT DEVICE AND METHOD FOR OPERATING SAME

(75) Inventor: Sukhwan Jun, Incheon (KR)

(73) Assignee: ALPINION MEDICAL SYSTEMS CO., LTD. (KR)

( * ) Notice: Subject to any disclaimer, the term of this patent is extended or adjusted under 35 U.S.C. 154(b) by 256 days.

(21) Appl. No.: 13/977,277

(22) PCT Filed: Dec. 7, 2011

(86) PCT No.: PCT/KR2011/009431
§ 371 (c)(1),
(2), (4) Date: Jun. 28, 2013

(87) PCT Pub. No.: WO2012/091315
PCT Pub. Date: Jul. 5, 2012

(65) Prior Publication Data
US 2013/0282040 A1 Oct. 24, 2013

(30) Foreign Application Priority Data
Dec. 28, 2010 (KR) .................. 10-2010-0136354

(51) Int. Cl.
*A61B 18/12* (2006.01)
*A61B 19/00* (2006.01)
*A61B 5/0205* (2006.01)
*A61N 7/02* (2006.01)
*A61B 17/32* (2006.01)
*A61B 18/00* (2006.01)

(52) U.S. Cl.
CPC ............... *A61B 19/50* (2013.01); *A61B 5/0205* (2013.01); *A61B 17/320068* (2013.01); *A61N 7/02* (2013.01); *A61B 2018/00839* (2013.01)

(58) Field of Classification Search
CPC ...... A61B 18/04; A61B 18/08; A61B 18/082; A61B 18/12; A61B 18/1206; A61B 18/1233; A61B 18/14; A61B 18/1442; A61B 18/1445; A61B 18/1477; A61B 18/1482; A61B 18/1485; A61B 18/1492; A61B 2018/0016; A61B 2018/0022; A61B 2018/00345; A61B 2018/00357; A61B 2018/00351; A61B 2018/00404; A61B 2018/00511; A61B 2018/00577; A61B 2018/00589; A61B 2018/00595; A61B 2018/0063; A61B 2018/00601; A61B 2018/00642; A61B 2018/00648; A61B 2018/00702; A61B 2018/00708; A61B 2018/00714; A61B 2018/00779; A61B 2018/00791; A61B 2018/00797; A61B 2018/00815; A61B 2018/00821; A61B 2018/00827; A61B 2018/00839; A61B 2018/00892; A61B 2018/00994; A61B 2018/126; A61B 2018/1467; A61B 2018/1475; A61B 2018/1495; A61B 2018/1861
USPC .................................................. 606/33–41
See application file for complete search history.

(56) References Cited

U.S. PATENT DOCUMENTS

| | | | |
|---|---|---|---|
| 2002/0169445 A1* | 11/2002 | Jain et al. ..................... | 606/41 |
| 2004/0153126 A1 | 8/2004 | Okai | |
| 2007/0083195 A1* | 4/2007 | Werneth et al. ............... | 606/41 |
| 2008/0188745 A1 | 8/2008 | Chen et al. | |
| 2010/0160781 A1 | 6/2010 | Carter et al. | |

FOREIGN PATENT DOCUMENTS

| | | |
|---|---|---|
| KR | 10-2006-0078207 A | 7/2006 |
| KR | 10-2007-0098856 A | 10/2007 |

OTHER PUBLICATIONS

International Search Report and Written Opinion (Both in Korean and English) for PCT/KR2011/009431, mailed Jul. 2, 2012; ISA/KR.

* cited by examiner

*Primary Examiner* — Michael Peffley
*Assistant Examiner* — Khadijeh Vahdat
(74) *Attorney, Agent, or Firm* — Harness, Dickey & Pierce, P.L.C.

(57) ABSTRACT

The present disclosure in some embodiments provides a medical device and to a method of operating the medical device. The medical device, comprising: a monitoring information processor configured to process and display cardiovascular information acquired through diagnosing or monitoring a target area of a patent body; a comparison unit configured to compare at least one values selected from the cardiovascular information with at least one threshold values; a cardiovascular information analysis unit configured to analyze the cardiovascular information provided depending on the result of comparison performed by the comparison unit and to produce an analysis result; and a therapeutic parameter setup unit configured to generate a setup information based on a part or all of the cardiovascular information and the analysis result and to generate therapeutic pulses for adjusting a level of a treatment on the patient body according to the setup information.

7 Claims, 6 Drawing Sheets

TREATMENT DEVICE AND METHOD FOR OPERATING SAME

TECHNICAL FIELD

The present disclosure in some embodiments relates to a medical device and to a method of operating the same. More particularly, the present disclosure relates to a medical device capable of adjusting a patient's treatment level in a high-intensity focused ultrasound (HIFU) treatment, for example, with the use of cardiovascular information such as a blood flow velocity, a blood flow rate and the like, and to a method of operating the medical device.

BACKGROUND

The statements in this section merely provide background information related to the present disclosure and may not constitute prior art.

An ultrasonic wave or ultrasound diagnosis and treatment of human body are under active research and development because it obviates the need for an incision of a human body and thus leaves neither a surgical scar nor the concern for secondary infections in general. Exemplary applications of the ultrasonic wave or ultrasound for the medical field are a diagnosis area such as a fetal diagnosis or a cancer diagnosis and a treatment area such as a lipectomy or destruction of a cancer tissue or malignant tumor.

A HIFU (High-Intensity Focused Ultrasound) is a surgical treatment of burning cancer cells by intensively irradiating the ultrasonic wave on a cancer tissue. Although the HIFU has been known to be developed for treating a prostate cancer, it is gradually extending its applications to a non-solid tumor such as a brain cancer, a uterine myoma and an arrhythmia beyond a solid cancer such as a liver cancer, a breast cancer and a pancreatic cancer and the like. Especially, the HIFU treatment now presents an excellent result in the treatment of a liver cancer and a pancreatic cancer for which a surgical operation is scarcely applicable.

The HIFU treatment has various aspects such as a thermal effect, a cavitation effect, a mechanical effect, a capillary destruction nearby a tumor and an immunity effect. Herein, the thermal effect includes the coagulation of a blood vessel and the necrosis of tumor cells by use of heat above 65 degrees; and the cavitation effect is related to pressurizing cells to cause cell protein to be denatured and thereby destroying DNAs of the tumor. In addition, the mechanical effect is to break the chemical link between cancer cells. The capillary destruction adjacent to the tumor is to prevent the tumor from proliferating by destroying the adjacent capillary so as not to supply nutrition to the tumor as well as a lesion to be treated, and the immunity effect relates to increasing the level of immunity as with increasing lymphocyte by recognizing the tumor cell destroyed after the treatment as an antigen. Among these effects, the thermal effect is one of the most popular kinds.

However, the thermal treatment using the HIFU entails thermal diffusions due to blood flows, resulting in mistimed and/or inadequate treatments.

DISCLOSURE

Technical Problem

The present disclosure has been made to provide a medical device capable of adjusting a patient's treatment level in a HIFU treatment, for example, with the use of cardiovascular information such as a blood flow velocity or a blood flow rate, and to a method of operating the medical device.

SUMMARY

At least one embodiment of the present disclosure provides a medical device, comprising: a monitoring information processor configured to process and display cardiovascular information acquired through diagnosing or monitoring a target area of a patent body; a comparison unit configured to compare at least one values selected from the cardiovascular information with at least one threshold values; a cardiovascular information analysis unit configured to analyze the cardiovascular information provided depending on the result of comparison performed by the comparison unit and to produce an analysis result; and a therapeutic parameter setup unit configured to generate a setup information based on a part or all of the cardiovascular information and the analysis result and to generate therapeutic pulses for adjusting a level of a treatment on the patient body according to the setup information.

Another embodiment of the present disclosure provides a method for operating a medical device, comprising: processing and rendering cardiovascular information acquired through diagnosing or monitoring a target area of a patient body; comparing at least one values selected from the cardiovascular information with at least one threshold values; analyzing the cardiovascular information provided depending on the result of comparison performed by the comparison unit and producing an analysis result; and generating a setup information based on a part or all of the cardiovascular information and the analysis result and generating therapeutic pulses for adjusting a level of a treatment on the patient body according to the setup information

ADVANTAGEOUS EFFECTS

According to the present disclosure, the treatment time can be reduced by controlling a thermal diffusion due to the blood flow during the HIFU treatment and the treatment performance can be maximized by using the cardiovascular information such as the heart rate, the blood pressure and the SpO2 as well as the blood flow information of the treatment part or the organ during the HIFU treatment.

In addition, the efficiency of the medical device can be improved since apparatuses for acquiring the cardiovascular information during the HIFU treatment can be implemented on a single system.

DETAILED DESCRIPTION

Hereinafter, a detailed description is given with reference to accompanying drawings.

Figure 1:
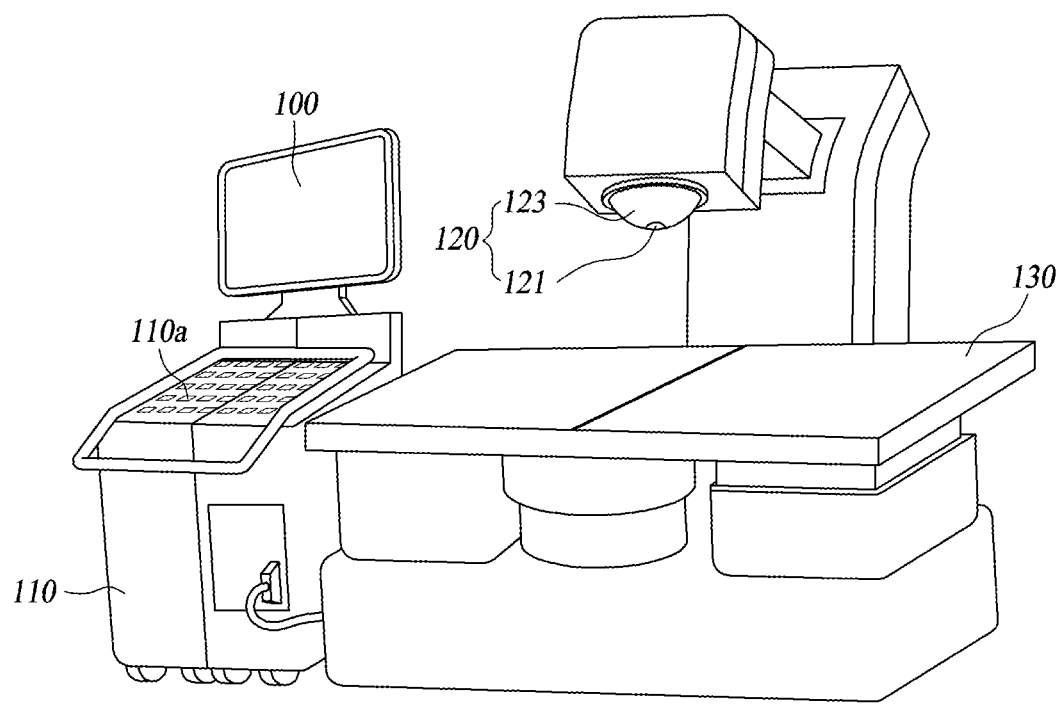
FIG. 1 is an exemplary diagram of a medical device according to at least one embodiment.

FIG. 1 is a diagram schematically showing a medical device according to one or more embodiments of the present disclosure.

Referring to FIG. 1, the medical device according to one or more embodiments of the present disclosure includes a display unit 100, a controller body 110 and a treatment unit 120, and may further include a treatment table 130 on which a patient is placed for treatment or diagnosis and a measuring device (not shown) for obtaining physiologic signals such as an electrocardiogram (ECG), a heart rate, a blood pressure and a saturation of percent of oxygen ($SpO_2$) of the patient.

Herein, the display unit 100 is a display device like a computer monitor. The display unit 100 may display not only patient's physiologic signals such as a blood flow velocity and/or rate provided upon acquiring from a monitoring unit 121 but also other physiologic signals including ECG, heart rate and blood pressure acquired through a separate measuring apparatus such as an ECG measuring apparatus and a blood pressure measuring apparatus. The display unit 100 further displays patient's additional information inputted to a patient monitoring module (not shown) by a hospital medical team or the operations staff or provided on-line over a connection with e.g., a server of another medical institution. The display unit 100 can also display the treatment result of a patient.

A controller body 110 may include a key input unit 110a for manipulating user interfaces for diagnosis or treatment. It controls and manages processes such as processing information on a patient's blood flow change monitored in real time through the monitoring unit 121 and displaying the same on the display unit 100, and regulating the level or intensity of, for example, an ultrasonic irradiation through a therapeutic wave transmission unit 123 by analyzing the cardiovascular information of the patient acquired in real time. For example, when a measurement of the blood flow shows a large blood flow rate, an ultrasonic treatment may be temporally stopped, whereas the ultrasonic treatment may be performed intensively when the measurement shows a small blood flow rate. The controller body 110 can generate blood flow pattern information through analyzing a pattern such as a periodicity of a blood flow velocity since the blood flow may be different from one patient to another. Further, the controller body 110 may set up parameter information which helps different ultrasonic treatments to be administered for each specific patient and then carry out the specific treatment since the cardiovascular information such as ECG, blood pressure, heart rate and the $SpO_2$ are also available.

The treatment unit 120 includes a monitoring unit 121 and a therapeutic wave transmission unit 123. Herein, the monitoring unit 121 including e.g., a CCD camera acquires a reflected wave of a specific beam or a diagnosis pulse after it is transmitted on a specific part or area of a patient body. Herein, the acquired information may be supplied to the controller body 110. In this way, the monitoring unit 121 performs a real-time monitoring of the blood flow or its flow rate of the patient placed on the treatment table 130. In addition, for example, the therapeutic wave transmission unit 123 includes more than e.g., 512 channels of array elements configured to transmit ultrasonic waves or ultrasounds to provide a high power multi-focal outputs which are converged under the control of the controller body 110 and then irradiated on the therapy area of the patient body in high intensity.

Not shown in the drawings, the medical device according to one or more embodiments of the present disclosure further includes an additional measuring device such as a probe or a transducer for acquiring various physiologic signals or cardiovascular information such as an ECG, a blood pressure, a heart rate and a $SpO_2$ or the like.

Figure 2:
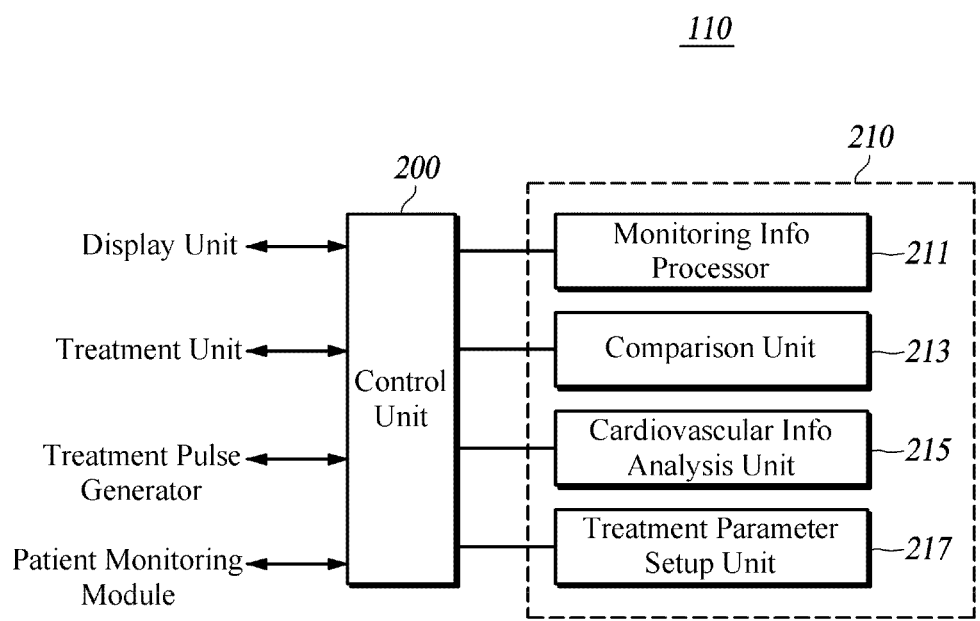
FIG. 2 is a block diagram of a configuration of a controller body of FIG. 1.

FIG. 2 is a block diagram of a configuration of a controller body of FIG. 1.

Referring to FIG. 2 together with FIG. 1, the controller body 110 according to one or more embodiments of the present disclosure includes a control unit 200 and a cardiovascular information processor 210 and further includes a therapeutic pulse generator (not shown) and a patient monitoring module (not shown).

The control unit 200 controls signals or information processed in the controller body 110. For example, the control unit 200 has a specific area of the patient's body monitored and renders the information related to the changes of blood flow and/or its rate to be displayed on the display unit 100 and thereby generates different therapeutic pulses depending on the analyzed cardiovascular information to treat the patient. For example, the control unit 200 commands the therapeutic pulse generator to generate and supply different therapeutic pulses to the therapeutic wave transmission unit 123 according to the setup information provided by the therapeutic parameter setup unit 217. Alternatively, using the setup information, the control unit 200 controls the output routes of the individually generated therapeutic pulses so as to appropriately supply the pulses to the therapeutic wave transmission unit 123.

The cardiovascular information processor 210 includes but not limited to a monitoring information processor 211, a comparison unit 213, a cardiovascular information analysis unit 215 and a therapeutic parameter setup unit 217.

Herein, the monitoring information processor 211 performs various signal processing methods on the cardiovascular information related to the patient's blood flow and/or its rate provided from the monitoring unit 121. In addition, the relevant information may be provided in the form of, e.g., a high resolution 3D image, to the display unit 100 under the control of the control unit 200. Further, the monitoring information processor 211 processes the cardiovascular information related to the ECG, blood pressure, heart rate and the like supplied through an additional measuring device as well as the cardiovascular information supplied from a patient monitoring module before supplying the information to the display unit 100. Herein, the patient monitoring module stores and manages the patient's cardiovascular information when it is supplied through separate input processes to the hospital medical team or the operations staff or provided on-line over a connection with e.g., a server of another medical institution.

The comparison unit 213 determines whether the cardiovascular information, e.g. the blood flow or its rate provided by the monitoring information processor 211 or a value derived from the cardiovascular information is below or above a threshold. Then, the determination results are supplied to the control unit 200. If it is above the threshold value, the control unit 200 is provided with the relevant result from the comparison unit 213 to stop the treatment session. The comparison unit 213 may also determine whether to stop the treatment after performing a comparison process with respect to a threshold value of the ECG or blood pressure. Further, if the temperature of liver is measured to be above a threshold value, the treatment may be controlled to terminate.

When the comparison unit 213 determines whether the cardiovascular information or its derived value to be equal to or smaller than a threshold value, the cardiovascular information analysis unit 215 receives the relevant information to analyze for the values of the blood flow and/or its rate per unit area and unit time. In addition, the cardiovascular information analysis unit 215 further includes the blood flow pattern analysis unit which figures out the pattern of the blood flow of the patient, i.e., the increment of the blood flow velocity during what period or time unit. Further, the cardiovascular information analysis unit 215 may additionally analyze various cardiovascular information such as the ECG, the blood pressure, the heart rate and the $SpO_2$ and the like supplied from the patient monitoring module and further analyze the cardiovascular information such as the ECG, the blood pressure and the heart rate and the like supplied from another measuring device.

The therapeutic parameter setup unit 217 sets correlation information for use in controlling the treatment level or intensity of the patient depending on the information analyzed by the cardiovascular information analysis unit 215. For example, the information subject to settings includes one which either permits the use of parameters associated with the blood flow and/or its rate and the parameter such as the ECG and the heart rate among the cardiovascular information or permits the use of parameters such as the temperature of a specific organ such as a liver. For example, when the therapeutic parameter setup unit 217 provides set information based on the blood flow/rate-related parameter, the control unit 200 may perform treatment of the patient by generating variable therapeutic pulses depending on the set information. To this end, the therapeutic parameter setup unit 217 may store and manage the set information in the form of a lookup table.

Figure 3:
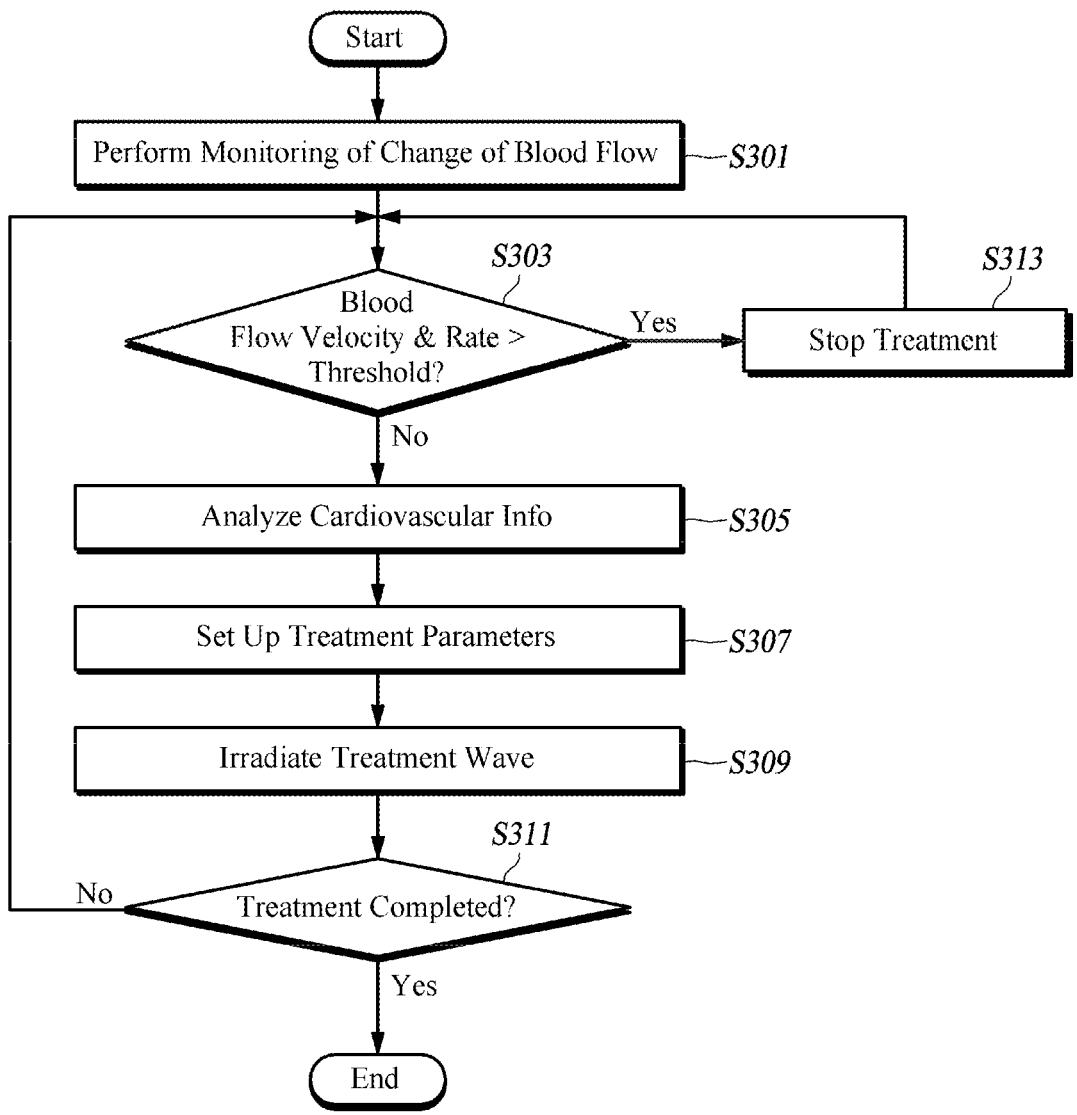
FIG. 3 is a flowchart of procedures of the operation of the medical device of FIG. 1.
Figure 4A:
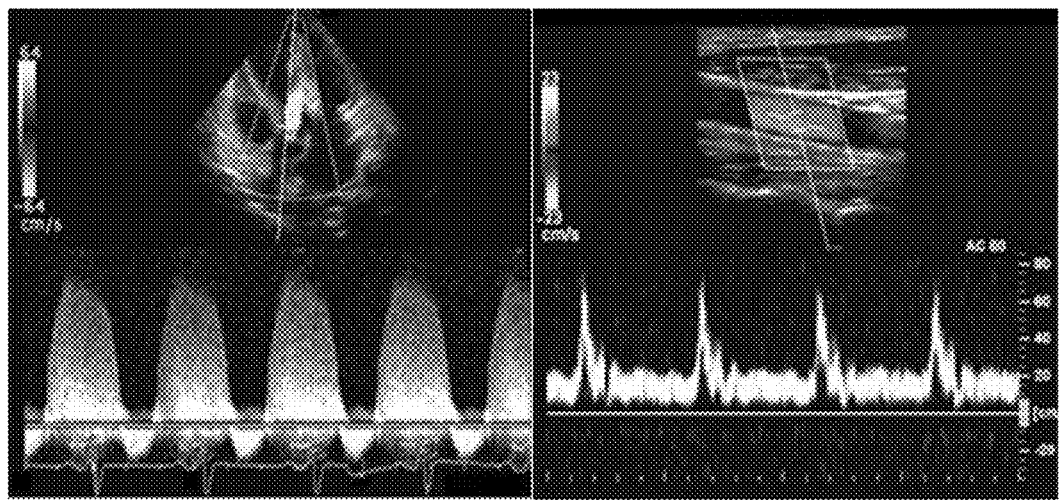
FIGS. 4A to 4D are schematic diagrams of the procedures of FIG. 3.
Figure 4B:
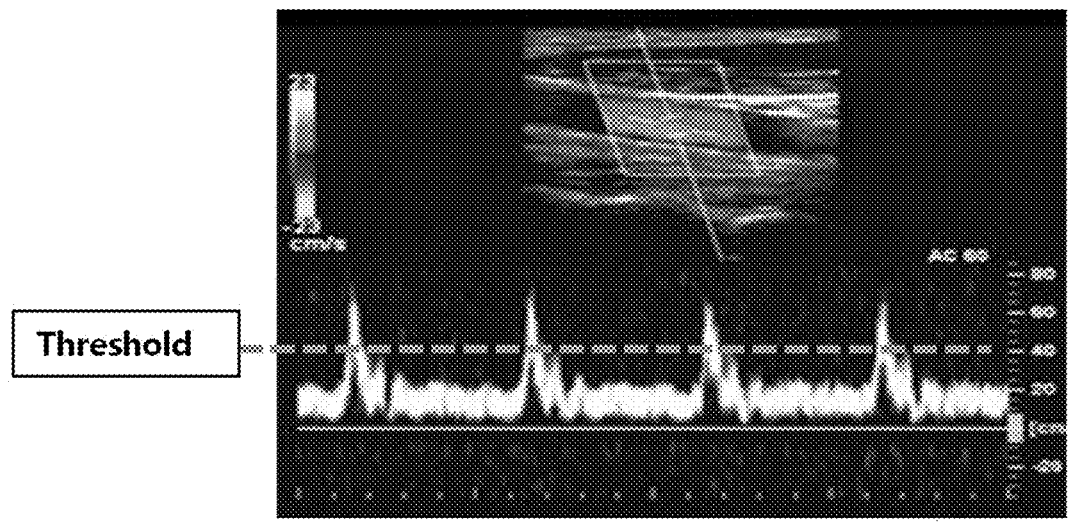
Figure 4C:
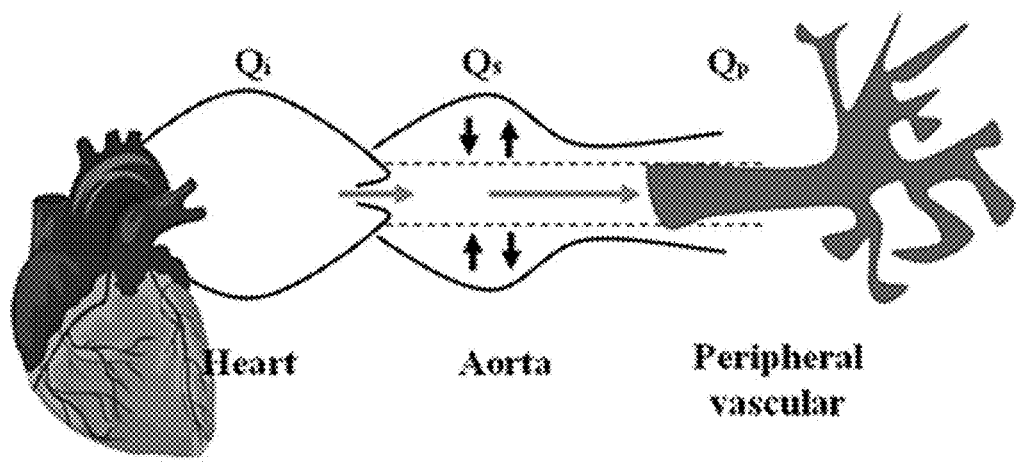

FIG. 3 is a flowchart of operating procedures of the medical device of FIG. 1; and FIGS. 4A to 4C are schematic diagrams of the procedures of FIG. 3.

Referring to FIG. 3 and FIGS. 4A to 4C together with FIG. 1 and FIG. 2, the medical device performs monitoring with a view to obtaining the cardiovascular information of a patient placed on a treatment table 130 (at step S301). The cardiovascular information such as the real-time blood flow and/or its rate acquired through such monitoring can be presented as FIG. 4a.

Then, the medical device determines whether the monitored cardiovascular information, e.g., the blood flow and/or its rate, is above or below the threshold value as shown in FIG. 4b (S303). The medical device may be operated to stop treatment if available in response to, for example, a large blood flow to thereby minimize an excessive thermal diffusion due to the large blood flow.

When the blood flow and/or its rate is determined to be lower than the threshold, the medical device receives and analyzes the cardiovascular information (S305). For example, in order to measure the blood flow and/or its rate of the blood supplied to the capillaries from the heart as shown in FIG. 4c, the medical device measures the blood flow rate per unit area and per unit time, and it may utilize the Doppler effect for the measurement of the changes of the blood flow and/or its rate. In this process, the medical device can also analyze the pattern of the blood flow velocity for each patient. In other words, since the heart repeats relaxation and contraction with a constant periodicity, an analysis is performed to figure out differences in periods of blood supply for each patient.

Subsequently, the medical device performs a parameter-setting process for treatment parameters by using a part or all of the cardiovascular information and information obtained by analyzing the cardiovascular information (S307). Herein, the parameter-setting process may refers exemplarily to a process that, in case of using information related to the blood flow and/or its rate, performs matching those information to with information freshly stored in a memory, or that reads out fresh information which will be used to control the treatment level of the patient according to the cardiovascular information or the analyzed information. To this end, the embodiment of the present disclosure may arrange the fresh information to be read out through the matching of the related information in the form of a lookup table.

Figure 4D:
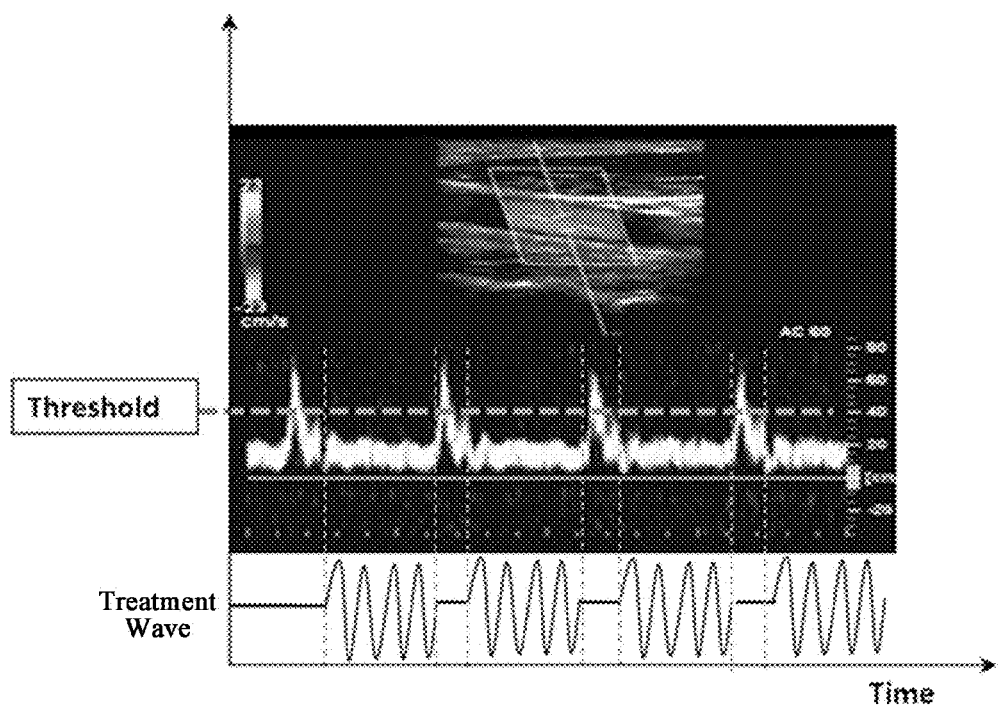

The medical device performs treatment by transmitting the therapeutic pulses such as an ultrasonic wave or ultrasound at a controlled treatment level pursuant to such set information (S309). The medical device proceeds with performing the treatment of the patient mainly when the blood flow rate is small and the blood flow velocity is slow, as shown in FIG. 4d. It may adjust in real time the treatment level which is controlled for each patient according to the setup information during the treatment.

Thereafter, the medical device determines whether a prescribed treatment time has passed or not (S311), by which time the treatment is performed according to the information being monitored in real time. When the prescribed treatment time has lapsed, the treatment process may be made to end.

On the other hand, if the blood flow and/or its rate is larger than the threshold value in the step S303, the medical device may repeat the process of temporarily pausing the on-going respective treatment (S313).

Figure 5:
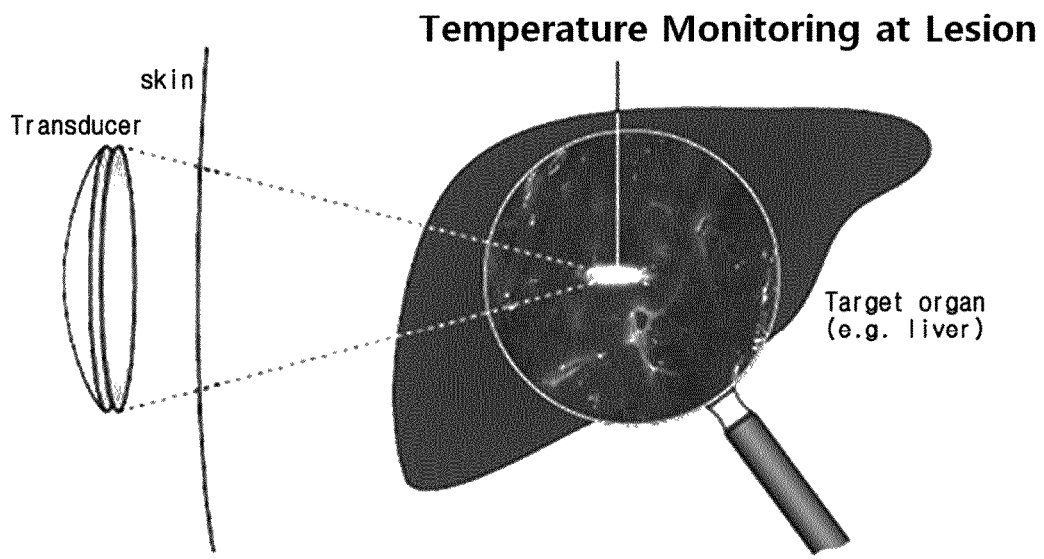
FIG. 5 is a diagram of a treatment process on a liver with temperature monitoring according to at least one embodiment.
Figure 6:
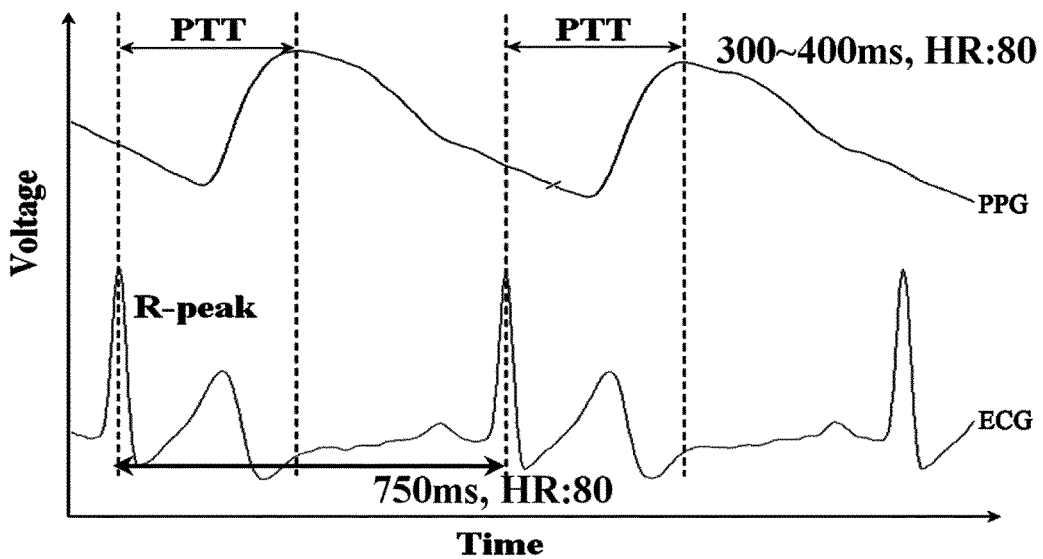
FIG. 6 is an exemplary diagram of using characteristics of electrocardiogram (ECG) and photoplethysmography (PPG) signals as cardiovascular information according to at least one embodiment.

FIG. 5 is a diagram of a treatment process on a liver with temperature monitoring according to at least one embodiment; and FIG. 6 is an exemplary diagram of using characteristics of electrocardiogram (ECG) and photoplethysmography (PPG) signals as cardiovascular information according to at least one embodiment.

As shown in FIG. 5, the medical device according to one or more embodiment of the present disclosure is capable of full control over the treatment level or intensity according to the temperature characteristics upon monitoring of the temperature of a specific organ such as a liver. For example, a high-intensity focused ultrasonic wave or ultrasound is irradiated on the therapy target area of the liver, and if the measured result of the temperature of the liver exceeds a prescribed threshold value, the treatment can be made to pause or the irradiation level of the ultrasonic wave or ultrasound can be made to drop for a time being before resuming the level to the treatment when the temperature gets below the threshold value.

As shown in FIG. 6, the medical device according to one or more embodiments of the present disclosure may proceed with the ultrasonic wave treatment by using the ECG and PPG signals. For example, if a measurement of the ECG and the pulse through the patient's finger or other body parts by using an additional measuring device shows the ECG and PPG signal characteristics as illustrated in FIG. 6, the ultrasound treatment can be made to stop at an arbitrary time within a period or the treatment can be made to continue but with a controlled level of the ultrasonic wave. For example, the present invention can treat the patient by irradiating the therapeutic pulses with various level of intensities.

Except the above descriptions of FIGS. 5 and 6, the medical device by this embodiment of FIGS. 5 and 6 is similar to the medical device and the method of operating the same explained with reference to FIG. 1 to FIG. 3 and FIG. 4a to FIG. 4d, and the detailed explanation will not be repeated.

In the description above, although all of the components of the embodiments of the present disclosure may have been explained as assembled or operatively connected as a unit, one of ordinary skill would understand the present disclosure is not limited to such embodiments. Rather, within some embodiments of the present disclosure, the respective components are selectively and operatively combined in any number of ways. Those skilled in the art will appreciate that various modifications, additions and substitutions are possible, without departing from the essential characteristics of the disclosure. Therefore, exemplary embodiments of the present disclosure have been described for the sake of brevity and clarity. Accordingly, one of ordinary skill would understand the scope of the disclosure is not limited by the explicitly described above embodiments but by the claims and equivalents thereof.

INDUSTRIAL APPLICABILITY

As the embodiments of the present disclosure are applicable to a medical device and a method for operating the same. According to the embodiments of the present disclosure, for example, the treatment time can be reduced by minimizing the thermal diffusion due to the blood flow during a HIFU treatment and the treatment effect can be maximized by using additional cardiovascular information such as the heart rate, the blood pressure and the SpO2 as well as the blood flow information of the therapy area or the organ during the HIFU treatment. In addition, the overall efficiency of the medical device can be improved since the apparatuses for acquiring the cardiovascular information during the HIFU treatment can be implemented on a single system.

CROSS-REFERENCE TO RELATED APPLICATION

If applicable, this application claims priority under 35 U.S.C §119(a) of Patent Application No. 10-2010-0136354, filed on Dec. 28, 2010 in Korea, the entire content of which is incorporated herein by reference. In addition, this non-provisional application claims priority in countries, other than the U.S., with the same reason based on the Korean Patent Application, the entire content of which is hereby incorporated by reference.

The invention claimed is:

1. A medical device, comprising:
a therapeutic pulse generator configured to generate therapeutic pulses;
a monitoring information processor configured to process and display cardiovascular information acquired through diagnosing or monitoring a target area of a patient body, the cardiovascular information including a blood flow rate or a blood flow velocity of the patient measured in real-time with a monitoring unit;
a comparison unit configured to compare a value extracted from the cardiovascular information with a threshold values, wherein said value extracted from the cardiovascular information is the blood flow rate or the blood flow velocity of the target area;
a cardiovascular information analysis unit configured to analyze the cardiovascular information to produce an analysis result including a periodicity of a blood flow of the target area;
a therapeutic parameter setup unit configured to generate a setup information based on at least one of the cardiovascular information or the analysis result, wherein the setup information is associated with adjusting a level of treatment on the patient body; and
a control unit configured to control the therapeutic pulse generator based on the setup information and to make the therapeutic pulse generator stop or reduce the generation of the therapeutic pulses while said value extracted from the cardiovascular information is larger than the threshold value in each cycle of blood flow of the target area, thus to avoid heat diffusion into adjacent tissues caused by blood flow;
wherein:
the control unit is configured to stop or reduce the generation of the therapeutic pulses when the measured blood flow rate or blood flow velocity is equal to or greater than the threshold value; and
the control unit is configured to increase the generation of the therapeutic pulses when the measured blood flow rate or blood flow velocity is less than the threshold value.

2. The medical device of claim 1, further comprising:
the control unit further configured to perform control over the operations of the monitoring information processor, the comparison unit, the cardiovascular information analysis unit and the therapeutic parameter setup unit.

3. The medical device of claim 1, further comprising:
a therapeutic pulse generator being further configured to generate different therapeutic pulses according to the setup information.

4. The medical device of claim 1, further comprising:
a patient monitoring module configured to store and manage the cardiovascular information inputted by a medical personnel or another device over a network.

5. The medical device of claim 1, wherein the therapeutic parameter setup unit is in the form of a lookup table.

6. A method for operating a medical device, comprising:
processing and rendering cardiovascular information acquired through diagnosing or monitoring a target area of a patient body, the cardiovascular information including a blood flow rate or a blood flow velocity of the patient measured in real-time with a monitoring unit;
comparing a value extracted from the cardiovascular information with a threshold value, wherein said value extracted from the cardiovascular information is the blood flow rate or the blood flow velocity of the target area;
analyzing the cardiovascular information provided depending on the result of comparison performed by the comparison unit and producing an analysis result, the analysis result including a periodicity of a blood flow of the target area;
generating a setup information based on at least one of the cardiovascular information or the analysis result, wherein the setup information is associated with adjusting a level of a treatment on the patient body;
generating therapeutic pulses based on the setup information and stopping or reducing the generation of therapeutic pulses while said value extracted from the cardiovascular information is larger than the threshold value in each cycle of blood flow of the target area, thus avoiding heat diffusion into adjacent tissues caused by blood flow;
stopping or reducing the generation of the therapeutic pulses when the measured blood flow rate of blood flow velocity is equal to or greater than the threshold value; and
increasing the generation of the therapeutic pulses when the measured blood flow rate or blood flow velocity is less than the threshold value.

7. The method of claim 6, wherein the analyzing comprises, measuring a patient's change of blood flow using Doppler effect or measuring a periodicity of a blood flow of the patient.

* * * * *